United States Patent
Nathan et al.

(10) Patent No.: US 6,829,510 B2
(45) Date of Patent: Dec. 7, 2004

(54) SURFACE NEUROPROSTHETIC DEVICE HAVING AN INTERNAL CUSHION INTERFACE SYSTEM

(75) Inventors: Roger H. Nathan, Herzilia (IL); Amit Dar, Hashavim (IL)

(73) Assignee: Ness Neuromuscular Electrical Stimulation Systems Ltd., Raanana (IL)

( * ) Notice: Subject to any disclaimer, the term of this patent is extended or adjusted under 35 U.S.C. 154(b) by 0 days.

(21) Appl. No.: 10/155,179

(22) Filed: May 28, 2002

(65) Prior Publication Data

US 2003/0114892 A1 Jun. 19, 2003

Related U.S. Application Data

(60) Provisional application No. 60/340,277, filed on Dec. 18, 2001.

(51) Int. Cl.[7] .................................................. A61N 1/18
(52) U.S. Cl. ......................................... 607/149; 607/48
(58) Field of Search ............................. 607/48, 46, 49, 607/50, 115, 144, 149, 152

(56) References Cited

U.S. PATENT DOCUMENTS

| | | |
|---|---|---|
| 4,182,320 A | 1/1980 | Sweeney |
| 4,580,563 A | 4/1986 | Gross |
| 4,580,569 A | 4/1986 | Petrofsky |
| 4,697,808 A | 10/1987 | Larson et al. |
| 5,330,516 A | 7/1994 | Nathan |
| 5,507,836 A | 4/1996 | Pohlig |
| 5,628,722 A * | 5/1997 | Solomonow et al. ......... 607/48 |
| 5,643,332 A * | 7/1997 | Stein ............................ 607/49 |
| 5,695,452 A | 12/1997 | Grim et al. |
| 5,725,489 A | 3/1998 | Bar-Or et al. |
| 6,064,912 A * | 5/2000 | Kenney ....................... 607/48 |
| 6,179,800 B1 | 1/2001 | Torrens |

FOREIGN PATENT DOCUMENTS

WO    Wo 98/53877    5/1998    ............ A61N/1/04

OTHER PUBLICATIONS

Liberson et al; "Archives of Physical Medicine & Rehabilitation" Feb. 1961 p. 101–105.

* cited by examiner

*Primary Examiner*—George R. Evanisko
(74) *Attorney, Agent, or Firm*—Mark M. Friedman

(57) ABSTRACT

A surface neuroprosthetic device for functional electrical stimulation (FES) having an internal cushion interface system, and a method of using the device including: (a) an at least semi-rigid exoskeleton shell for covering at least a portion of a limb; (b) at least one cushion interface disposed between the shell and the limb, the cushion interface being directly attached to the shell, and (c) at least one electrical stimulation electrode associated with, and supported by, the cushion interface, wherein the cushion interface is configured to transfer pressure from the shell to the electrode, so as to provide electrical contact between the electrode and a skin surface of the limb, thereby effecting functional electrical stimulation of at least one muscle of the limb.

11 Claims, 8 Drawing Sheets

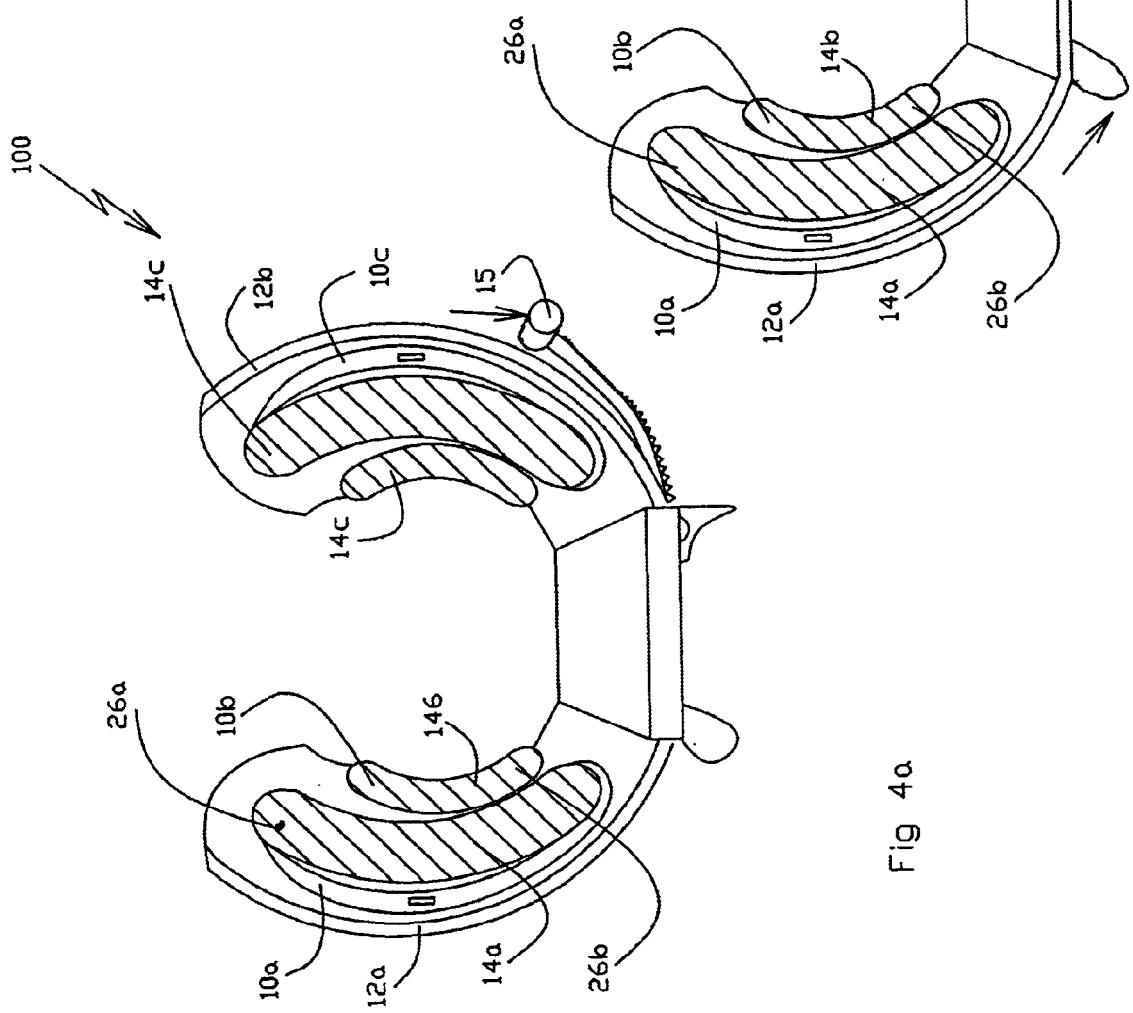

SURFACE NEUROPROSTHETIC DEVICE HAVING AN INTERNAL CUSHION INTERFACE SYSTEM

This patent application draws priority from U.S. Provisional Patent Application Ser. No. 60/340,277, filed Dec. 18, 2001.

FIELD AND BACKGROUND OF THE INVENTION

The present invention relates to neuroprosthetic devices, and more particularly, to a surface neuroprosthetic device having an internal cushion interface system for improved functional electrical stimulation.

It is known that movement impairment in a limb can result from various neurological or orthopedic pathological conditions, such as stroke, spinal cord injury, head injury, cerebral palsy and multiple sclerosis. Selected muscles of the impaired limb can be triggered to contract and to perform a controlled functional activity, such as walking and standing or grasping and lifting, by surface Functional Electrical Stimulation (FES). FES has been used both as a therapeutic modality and for the improvement or restoration of impaired activities.

Devices based on FES have been developed for activating specific body sites. Such devices for the lower limb include gait restoration and gait modification systems, such as the dropfoot system for activating the ankle joint, and systems that, in addition, activate the knee joint. Typical examples of devices for stimulating the lower limb are U.S. Pat. No. 4,697,808 to Larson, et al., and Liberson, et al., Arch. Phys. Med. and Rehabilitation, pp. 101–105 (February 1961). Other devices for the upper limb, such as U.S. Pat. No. 5,330,516 to Nathan, activate the hand, wrist, or elbow.

U.S. Pat. No. 5,330,516 teaches that to relieve regions of high localized pressure between a splint and a hand, semi-rigid padded plates may be inserted between the splint and the skin. This is particularly applicable to the dorsal surface of the hand, where splint/skin contact pressures are high during hand prehension. It must be emphasized that the purpose and function of these pads is to provide comfort, and not serve to support the electrodes, nor to promote the conforming of the electrode contact surface to the skin.

Additionally, there is a danger in known rigid and semi-rigid devices of pinching soft body-tissue between the shells while closing the device. This is particularly dangerous where sensory touch and pain feedback are impaired in various neurological pathologies.

U.S. Pat. No. 5,695,452 to Grim, et al., and U.S. Pat. No. 6,179,800B1 to Torrens are typical examples of a device imposing foam or padding between a shell surrounding a limb. Neither device is a FES device, nor do the devices include electrodes. U.S. Pat. No. 6,179,800B1 discloses a method of reduction of Colles' fracture, a specific type of wrist fracture. A splint includes first and second collars pivotally supported on a limb and adjustable to adjust the internal dimensions of the splint. The splint is provided with a support for supporting the extremity of the limb. Although the support allows some movement of the limb extremity, it is appreciated that the device is directed towards immobilization of the limb. By sharp contrast, neuroprosthetic devices require limb and muscle mobility, along with proper positioning of the electrodes against the contour of the skin surface, and maintaining sufficient and even electrode contact pressure as the contour changes with the contraction and relaxation of the stimulated muscles.

During activation of a limb or body site by a surface neuroprosthesis, the stimulation current flows through the electrode, through the skin and interposing biological tissues to the motor nerve, thereby activating the muscle. The effectiveness and comfort of a neuroprosthesis electrode is a complex issue, but is strongly influenced by the mechanical nature of the electrode-skin contact, as well other factors such as the electrical impedances of the electrode and skin component layers, the presence of any conductive liquid interposed between the electrode and skin, and the proximity to the stimulation site of target excitable tissue, and of afferent skin sensors.

The mechanical requirement at the electrode-skin interface is ideally an evenly-distributed pressure of sufficient magnitude depending on the magnitude of the current density being transmitted across the interface. Uneven pressure distribution can result in poor conduction of the stimulation current over a portion of the electrode and reduction in activation of excitable tissue under this electrode portion, together with an increase in the stimulation current density over other portions of the electrode. A high local concentration of the stimulation current density applied to the skin is referred to as a "hot spot" and is to be avoided in view of the discomfort or pain associated with passing such high intensity stimulation currents through the afferent skin sensors.

The result of uneven electrode—skin contact pressure will thus be unreliable and uncomfortable activation of the body limb.

U.S. Pat. No. 4,182,320 to Sweeney and U.S. Pat. No. 5,507,836 to Pohlig disclose inflatable or fluid-pressurized sleeves. U.S. Pat. No. 4,182,320 teaches a disposable, foldable and inflatable protective sleeve for a conventional, re-usable, rigid splint board. The sleeve is not a FES device.

U.S. Pat. No. 5,643,332 to Stein, and U.S. Pat. No. 4,580,563 to Petrofsky disclose FES devices. Neither device has a rigid or semi-rigid exoskeleton shell. U.S. Pat. No. 5,643,332 uses a flexible band, while U.S. Pat. No. 4,580,563 uses a cuff having a zipper for securing the cuff to a arm, thereby assuring that the electrodes are secured at place.

In understanding the requirements of the above-cited art, it must be emphasized that the neuroprosthesis requires the application of sufficient pressure to the regions of the electrodes. A sleeve, by definition, essentially encircles the body limb; such that elastic, pneumatic, or hydraulic pressure applied by the sleeve to the limb tends to compress substantially the whole limb circumference. The application of the requisite electrode contact pressure to the whole limb circumference can result in various deleterious effects such as discomfort, where the neuroprosthesis is in use for long periods, and impairment in the flow of biological fluids through the soft tissue of the limb. Reduction of the radial pressure exerted by the sleeve to allow unimpeded blood flow may result in insufficient electrode pressure, and consequently, partial loss of electrode contact.

A further barrier in the use of a soft elastic sleeve and the like is the requirement for the hemiplegic patient having one plegic hand to don and doff the device. Because the soft elastic sleeve lacks structural rigidity, the patient is faced with mechanical problems, often insurmountable, in positioning the sleeve accurately and in fastening it securely on the limb using only one hand.

Thus, there is a recognized need for, and it would be highly advantageous to have, an internal cushion system for semi-rigid exoskeleton-type neuroprosthetic devices that, in addition to providing comfort, is convenient to don and doff, enables adaptive positioning of the electrodes, and provides both the requisite pressure at the electrode—skin interface and flexibility so as to substantially conform the electrode to the changing shape of the limb.

SUMMARY OF THE INVENTION

The present invention is a surface neuroprosthetic device having an internal cushion system. According to one aspect of the present invention, there is provided a surface neuroprosthetic device for functional electrical stimulation (FES) having an internal cushion interface system, the device including: (a) an at least semi-rigid exoskeleton shell for covering at least a portion of a limb; (b) at least one cushion interface disposed between the shell and the limb, the cushion interface being directly attached to the shell, and (c) at least one electrical stimulation electrode associated with, and supported by, the cushion interface, wherein the cushion interface is configured to transfer pressure from the shell to the electrode, so as to provide electrical contact between the electrode and a skin surface of the limb, thereby effecting functional electrical stimulation of at least one muscle of the limb.

According to further features in the described preferred embodiments, the cushion interface and local body tissue underlying the skin surface have a substantially similar modulus of elasticity.

According to still further features in the described preferred embodiments, the cushion interface is designed to conform to the skin surface during contraction and relaxation of muscles of the limb.

According to still further features in the described preferred embodiments, the cushion interface is designed to conform to the skin surface during articulations of the limb.

According to still further features in the described preferred embodiments, the cushion interface is configured to distribute interactive forces between the cushion interface and the skin surface, so as to maintain an essentially natural contour of the limb.

According to still further features in the described preferred embodiments, the cushion interface is designed to transfer pressure from the shell to the electrodes, such that an even pressure is applied to the skin surface, maintaining thereby operative contact between the electrodes and the surface.

According to still further features in the described preferred embodiments, the modulus of elasticity of the cushion interface is obtained using a solid filler material.

According to still further features in the described preferred embodiments, the cushion interface includes a compartment pressurized by a hydraulic fluid.

According to still further features in the described preferred embodiments, the cushion interface includes a compartment pressurized by air.

According to still further features in the described preferred embodiments, the exoskeleton shell is a rigid exoskeleton shell.

According to still further features in the described preferred embodiments, the exoskeleton shell is further designed and configured to be donned using a single hand.

According to still further features in the described preferred embodiments, the cushion interface includes an adaptive mechanical cushion.

According to still further features in the described preferred embodiments, the adaptive mechanical cushion has a substantially negligible damping constant.

According to still further features in the described preferred embodiments, the adaptive mechanical cushion has a damping constant sufficiently low such that the electrode maintains dynamic contact with the surface during contraction and relaxation of muscles of the limb.

According to still further features in the described preferred embodiments, the device further includes adjusting means for attaching the adaptive mechanical cushion to the shell, so as to allow adjusting a distance between the adaptive mechanical cushion and the shell, permitting, thereby, continuous and effective contact between the electrode and the surface.

According to still further features in the described preferred embodiments, the device further includes a mechanism for opening and closing of the neuroprosthetic device, wherein the mechanism is configured to transfer pressure from the shell to the cushion so as to avoid pinching of a soft tissue of the limb as the device is donned and doffed.

According to still further features in the described preferred embodiments, the mechanism is a linear closure mechanism.

According to still further features in the described preferred embodiments, the adaptive mechanical cushion includes at least one mechanical spring, associated with the shell, for providing a pre-determined effective modulus of elasticity.

According to still further features in the described preferred embodiments, the device further includes a mechanism for reversible opening and closing of the neuroprosthetic device, the mechanism being configured to transfer pressure from the shell to the adaptive mechanical cushion so as to avoid pinching of a soft tissue of the limb.

According to still further features in the described preferred embodiments, the device further includes elastic straps operatively connected to the shell, and wherein the electrode is connected to the straps, such that closing of the mechanism tensions the elastic straps so as to press the electrode to the surface of the limb.

According to still further features in the described preferred embodiments, the surface of the cushion interface system is affixed to the exoskeleton shell, the surface of the cushion system having a substantially arc-like cross-section to interface with a body limb.

According to still further features in the described preferred embodiments, the cushion interface is associated with the shell solely in regions of the surface of the cushion where electrodes are positioned.

According to another aspect of the present invention, there is provided a method of donning a neuroprosthetic device for functional electrical stimulation (FES), the device having an internal cushion interface system, the method including the steps of: (a) providing a surface neuroprosthetic device having: (i) an at least semi-rigid exoskeleton shell for covering at least a portion of a limb; (ii) at least one cushion interface disposed between the shell and the limb, the cushion interface being directly attached to the shell, and (iii) at least one electrical stimulation electrode associated with, and supported by, the cushion interface, (b) covering the portion of the limb with the neuroprosthetic device so as to transfer pressure from the exoskeleton shell to the electrode, thereby providing electrical contact between the electrode and a skin surface of the limb, so as to effect functional electrical stimulation of at least one muscle of the limb.

According to further features in the described preferred embodiments, step (b) of the method is performed with a single hand.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 4a is a side view of another embodiment of a neuroprosthetic device having an adaptive mechanical cushion system, the device shown in a closed position;

FIG. 4b is a side view of the device of FIG. 4a, shown in an open position;

FIGS. 6a–6c are schematic, sectional view of a fluid-filled cushion interfaces for use in conjunction with the inventive neuroprosthetic device, wherein:

FIG. 6a is a pneumatic cushion interface that fluidly communicates with the environment;

FIG. 6b is a pneumatic cushion interface having a trapped, pressurized fluid volume, and FIG. 6c is a pneumatic cushion interface having a closed, pressurized fluid volume in fluid communication with a pump.

DESCRIPTION OF THE PREFERRED EMBODIMENTS

Figure 1:
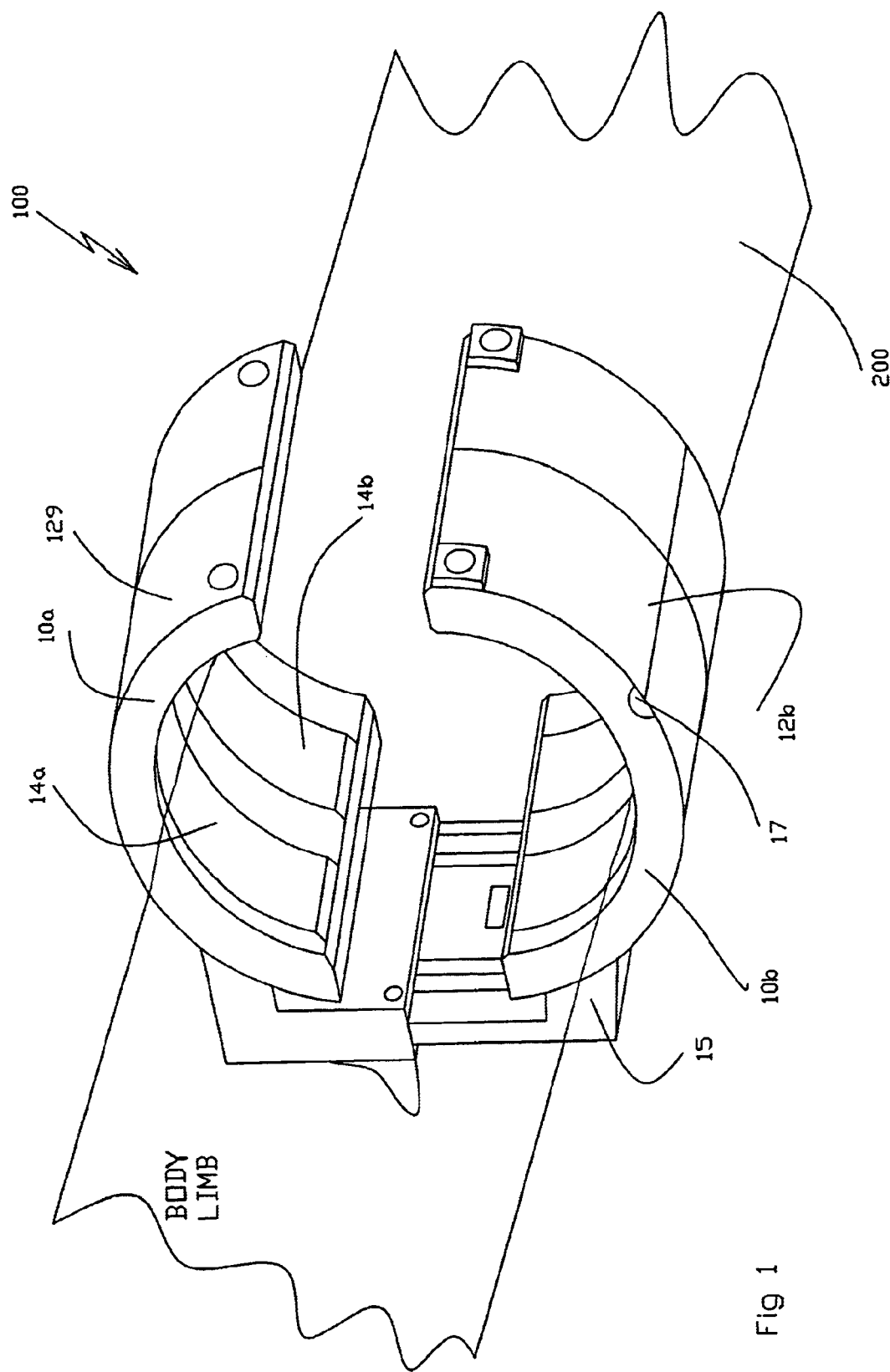
FIG. 1 is a perspective view of a neuroprosthetic device of the present invention, having a shell and a soft internal cushion system.

The present invention is a neuroprosthetic device for impaired limbs having an internal cushion system. The principles and operation of the system according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

Figure 2:
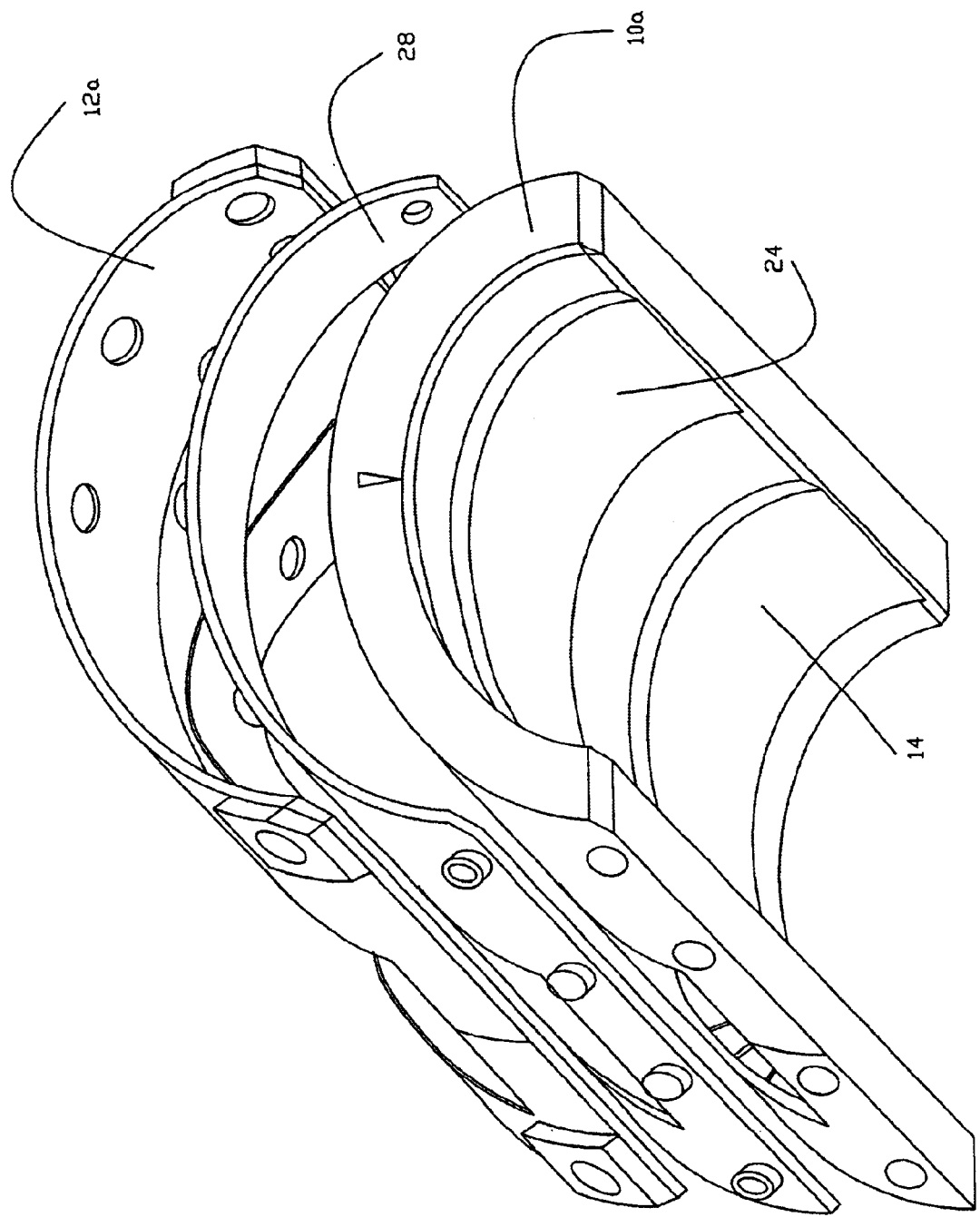
FIG. 2 is an exploded perspective view of the cushion system assembly of FIG. 1.
Figure 5B:
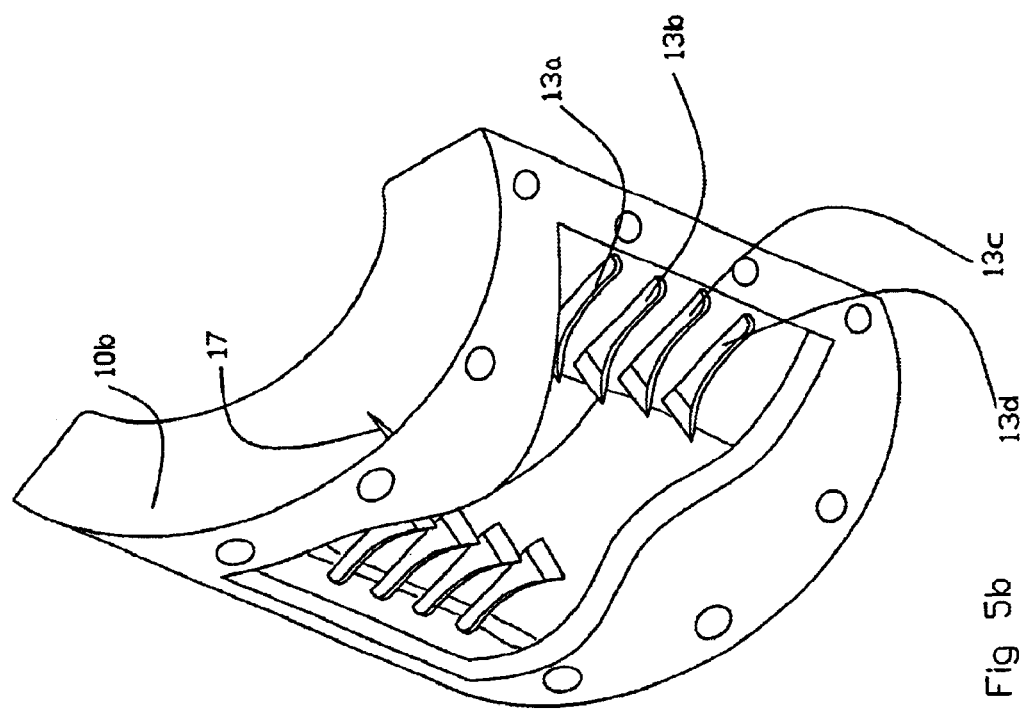
FIG. 5b is a schematic perspective rear view of the cushion system of FIG. 1.
Figure 5A:
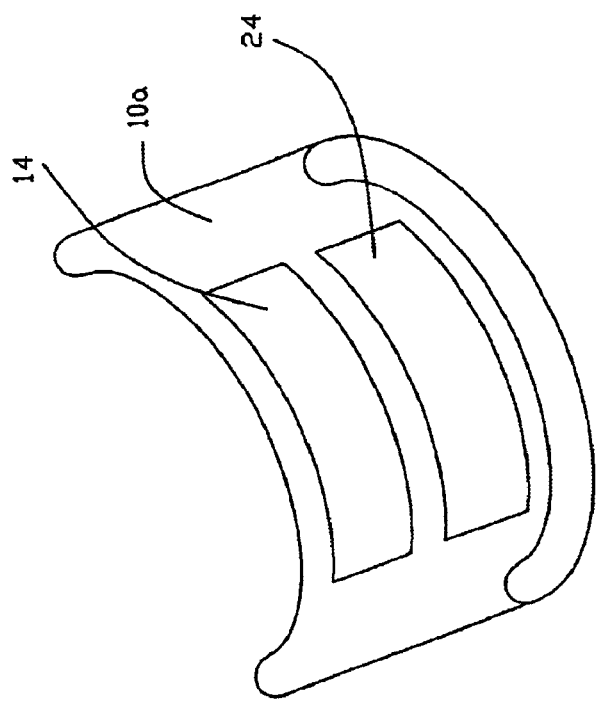
FIG. 5a is a schematic perspective view of the cushion system of FIG. 1.

Referring now to the drawings, FIGS. 1, 2, and 5a–5b illustrate a neuroprosthetic device having a rigid or semi-rigid exoskeleton shell and an internal cushion system. FIG. 1 is a schematic perspective view of the device 100, shown in place on a portion of body limb 200. FIG. 2 is an exploded perspective view of the shell and internal cushion system of FIG. 1. FIG. 5a is a schematic perspective view of the cushion system of FIG. 1, without the shell, and FIG. 5b is a schematic perspective rear view of the cushion system.

In the above-referenced drawings, soft cushions 10a and 10b are interposed between exo-skeleton shells 12a and 12b of neuroprosthetic device 100 and the skin surface of limb 200. Exoskeleton shells 12a and 12b are rigid or semi-rigid. Preferably, exoskeleton shell 12a is attached to cushion 10a by means of connection frame 28 disposed therebetween, as best seen in FIG. 2. Exo-skeleton shells 12a and 12b and cushions 10a and 10b substantially envelop the circumference of the limb, and have specific mechanical properties, geometry and materials of construction, which are detailed hereinbelow.

An important feature of the present invention is that internal cushions 10a and 10b have a modulus of elasticity similar to that of the soft tissue of the body. The modulus of elasticity of the cushion preferably lies within the range of approximately 100–500 Pa, depending on the nature of the underlying soft tissue at the body site. Substantially higher values of the modulus may cause excessive local soft tissue deformation, while substantially lower values of the modulus may result in insufficient electrode contact pressure.

The viscosity of the cushion should be substantially negligible, as any viscosity can only be detrimental to the requirement for intimate electrode/skin contact. A viscosity of 100 Pa/s should not be exceeded, and lower viscosities are highly preferable.

Thus, in contrast to prior art devices, the pressured positioning of neuroprosthetic device 100 against the limb causes cushions 10a and 10b to deform, such that the interactive forces with the skin are well distributed, and a firm, even pressure is applied over the region where electrodes 14 and 24 are positioned, even during changes in limb topography resulting from muscle contraction and relaxation and from limb articulations.

Additionally, semi-rigid exo-skeleton shells 12a and 12b and cushions 10a and 10b are preferably wrapped around the circumference of the limb so as to allow for variations in limb diameter from individual to individual. This is facilitated by the deformation of cushions 10a and 10b and by the (preferably linear) closure of closure mechanism 15.

According to further embodiments of the present invention, cushions 10a and 10b are hollow, fluid-filled, or filled with an elastic substance having an appropriate modulus of elasticity, such as certain soft sponges. It will be appreciated that sponge materials are extremely varied and have a correspondingly-wide range of elasticity. Hence, many sponge materials, and hard or dense sponge materials in particular, are generally unsuitable or of reduced efficacy for most soft-tissue areas of the body. The preferred sponge material is selected to match the elastic properties of the limb soft tissue at the neuroprosthesis site.

The required elastic properties of cushions 10a and 10b are satisfied in the preferred embodiment by the inherent bending resistance of the structural walls of cushions 10a and 10b. Alternatively, the inherent bending resistance may be augmented by the inclusion of ribs 13a–13d, which are beam structures within cushions 10a and 10b. Local thickening of cushion walls may also stiffen cushions 10a and 10b where required. Similarly, the cushion structure may be softened by local thinning or weakening of the walls. FIG. 5d shows the cushion corners weakened with slits 301.

Figure 5C:
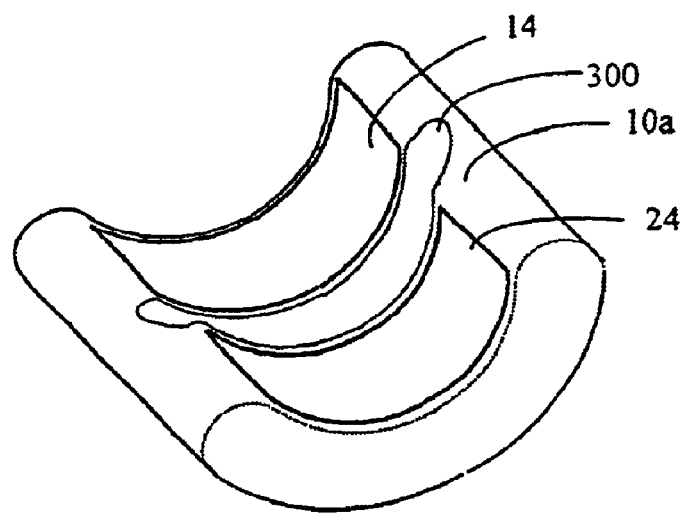
FIG. 5c is a schematic perspective view of a preferred embodiment of the inventive cushion system having a partially-recessed interior facing.
Figure 5D:
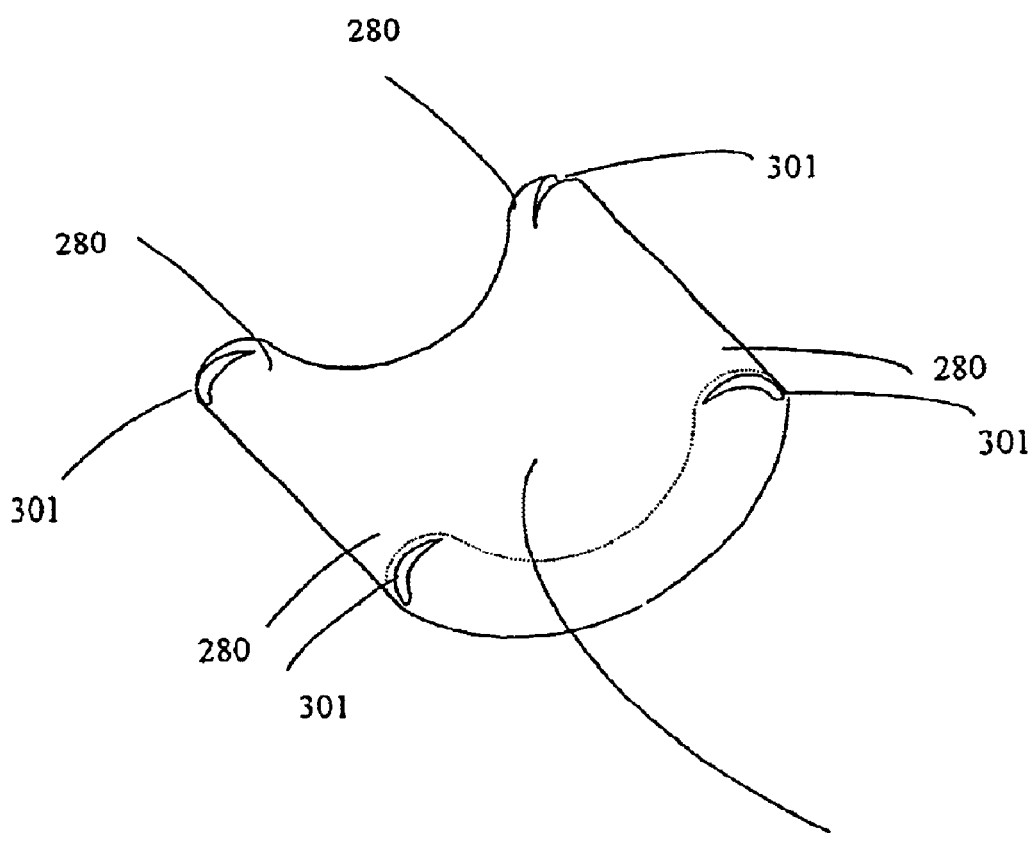
FIG. 5d is a schematic perspective view of a preferred embodiment of the inventive cushion system having slit corners.

FIG. 5c provides a schematic perspective view of a preferred embodiment of the inventive cushion system having an interior facing that has a recess 300 disposed between electrodes 14 and 24. Recess 300 effectively reduces the pressure region on the limb, relieving the cushion interactive pressure from any region not covered by an electrode.

Preferably, the configuration of shells 12a and 12b and internal cushions 10a and 10b is anatomically contoured such that the inside surface of closed neuroprosthetic device 100 corresponds to the external surface of a typical plegic limb, in mid-range position.

During the donning of device 100, cushions 10a and 10b deform from resting shape due to the interaction with the body tissue. The deformation of the surface of cushions 10a and 10b during the donning process guides the soft tissue and enables the tissue to be arranged appropriately within device 100. For example, in closing exo-skeleton shells 12a and 12b on the limb using closure mechanism 15, the surfaces of cushions 10a and 10b are retracted, along with the soft tissue, from the moving parts of closure mechanism 15, thereby reducing the danger of pinching between rigid moving parts. Closure mechanism 15 is preferably a linear closure mechanism, which has been found to be superior to various jaw-type mechanisms.

External shells 12a and 12b and internal cushions 10a and 10b enable proper and intimate contact of electrodes 14 and 24 on the skin by applying a uniform and sufficient pressure to electrodes 14 and 24 on the surface of limb 200 while enclosing and holding the tissue mass of limb 200 in device 100.

Internal soft cushions 10a and 10b conform to the general size and contour of the body limb to which it applied and, in addition, to local changes in the shape of the muscles of the limb during contraction and relaxation and joint articulation.

Some neuroprosthesis devices of the prior art (e.g., U.S. Pat. No. 5,330,516) have a semi-rigid exoskeleton, yet are functional without a cushion interface system interposed between the exoskeleton panels and the body site. It must be emphasized, however, that in such devices, an intimate electrode-skin contact is maintained by deforming the limb soft tissue locally to conform to the shape of the exoskeleton panel, at least in the region of the electrodes. This deformation is achieved by applying sufficient pressure from the panel.

By sharp contrast, in the present invention, a cushion interface system is interposed to interface the soft tissue with the exoskeleton panel such that at least part of the local surface profile changes under the electrode region of the panel are provided by the cushion interface system. Hence, the local tissue deformation required to provide intimate electrode-skin contact can be reduced. The mechanical compliance of the cushion effectively allows a reduction in the resultant force applied to each electrode and hence allows a reduction in the total force that the exoskeleton panel must apply to the limb in order to ensure intimate electrode contact.

Moreover, at body sites where soft tissue layer thickness is large compared to local surface topographical changes during muscle contractions and limb articulations, the required tissue strains are relatively small. An example of such a site is the forearm dorsal surface, in which the surface topography is fairly stable relative to the thickness of the soft tissue layer, even during articulations of the hand and of the joints proximal and distal to the segment. However, the upper arm segment exhibits large profile changes, especially during flexion and extension of the elbow joint combined with activation of the biceps brachii and triceps brachii muscles. Applying sufficient pressure to deform the soft tissue to neutralize the large profile changes results in excessive force requirements between the exoskeleton and the limb.

Thus, although U.S. Pat. No. 5,330,516 to Nathan teaches an upper arm cuff, the efficacy of the device is limited. To date, a technologically and commercially viable product has not been produced, nor does such a device exist in the market, the great need for such a device notwithstanding.

The instant invention, by sharp contrast, provides a cushion interface system that delivers the correct mechanical compliance to imposed stress and strain interactions, significantly reducing thereby, the pressure required by the exo-skeleton panels to maintain an intimate electrode/skin contact.

Consequently, the system of the present invention avoids chronic tissue deformation that would impede the supply of metabolic substances to the limb, such as blood flow and distribution. This is achieved by reducing, preferably to a minimum, both the magnitude of the pressure applied by the cushion and the area over which the pressure is applied, and by avoiding, where possible, the application of pressure on major blood vessels and on other pressure-sensitive structures. The minimum pressure is that which provides contact of the skin with the entire surface of the electrode. Additional pressure is required to transfer comfortably the high intensities of stimulation currents typically used in neuroprosthesis applications.

The system of electrodes 14 and 24 is housed on the surface of cushions 10a and 10b facing inwards towards the treated limb. Electrodes 14 and 24 are permanently fixed to cushions 10a and 10b. Optionally, electrodes 14 and 24 are adjustable to allow their position relative to the exo-skeleton shells 12a and 12b to be modified or positioned individually for each patient according to individual needs.

In some embodiments of the present invention, cushions 10a and 10b, as well as electrodes 14 and 24, are replaceable, (or only electrodes 14 and 24), to permit simple periodical maintenance of the neuroprosthetic device 100. In many cases, it is desirable to have an opening for ventilation of sweat that may accumulate on the skin.

Figure 5F:
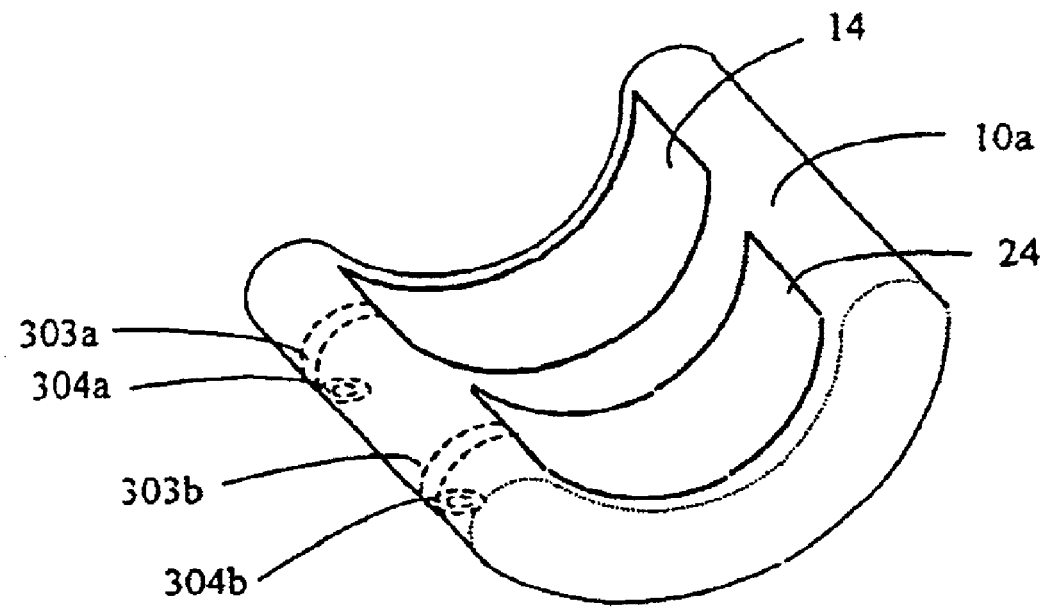
FIG. 5f is a schematic illustration of a preferred embodiment of the inventive cushion system having predefined, conductive electrode regions and predefined, substantially non-conductive regions.

In a preferred embodiment of the present invention, cushion 10a, shown in FIG. 5f, is preferably made from a non-conductive polymer such as silicon. Electrodes 14 and 24 are made from the same polymer material, but with a conductive component such as carbon or silver added to the material during the manufacturing process in predefined electrode regions. This renders cushion 10a conductive over the predefined electrode regions, and substantially non-conductive elsewhere. The conductive region may be extended on the back surface of the cushion to act as conductive leads 303a and 303b, to connect the electrode electrically with terminals 304a and 304b, which in turn connects to the electrical stimulation source (not shown).

Cushions 10a and 10b may be assembled in the device during the initial clinical set-up and fitting session. Cushion parameters can include size, shape, thickness, effective modulus of elasticity, electrode type, electrode position, and electrode size. The shape of cushions 10a and 10b may be right-limb or left-limb specific.

It will be appreciated by one skilled in the art that the electrodes (e.g., electrodes 14 and 24) can be positioned in different locations on the surface of the cushions (e.g., cushions 10a and 10b), in order to allow precise and accurate adjustment according to personal anatomical and neuro-physiological requirements and variables.

The three-dimensional structure of the cushion may provide the cushion with the requisite mechanical characteristics. As opposed to the simple, box-shaped structure of FIG. 5a, the structure of cushion 10a of FIG. 5d is weakened in each of corners 280 by a slit 301. The weakening of corners 280 reduces the effective modulus of elasticity of the structure to the desired level.

Figure 5E:
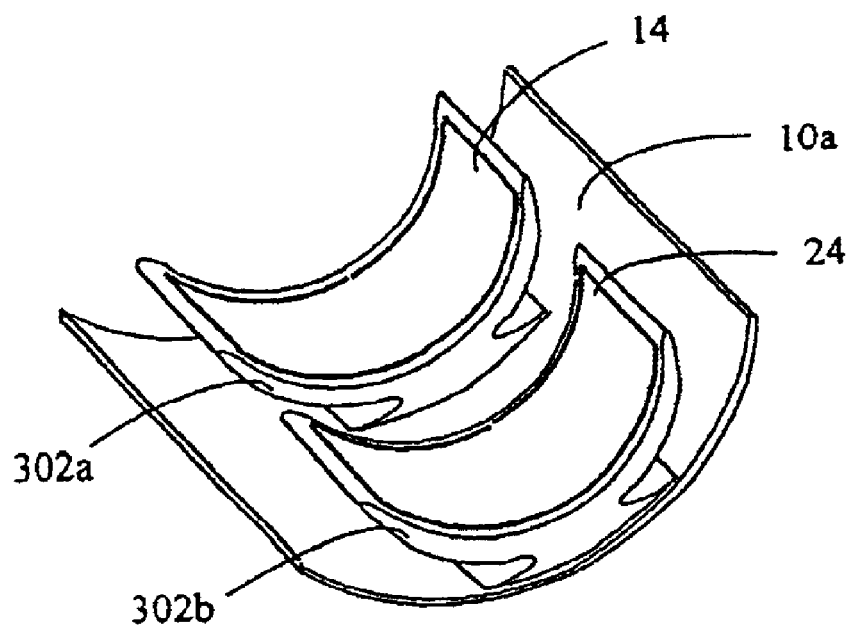
FIG. 5e is a schematic perspective view of a preferred embodiment of the inventive cushion system having a cantilever platform for supporting the electrode.

An additional variation is schematically provided in FIG. 5e. Electrodes 14 and 24 are mounted on individual platforms 302a, 302b, which act as cantilevers. This arrangement allows the effective modulus of elasticity of the structure to be reduced to a value within the range of soft tissue, as described hereinabove.

As used herein in the Specification and in the claims section that follows, the term "adaptive mechanical cushion" refers to mechanical assemblies including mechanical spring mechanisms such as spiral springs, leaf springs, tensile members, straps, and the like, which provide the inventive neuroprosthetic device with internal flexibility for adapting to the surface contours of a limb.

Figure 3:
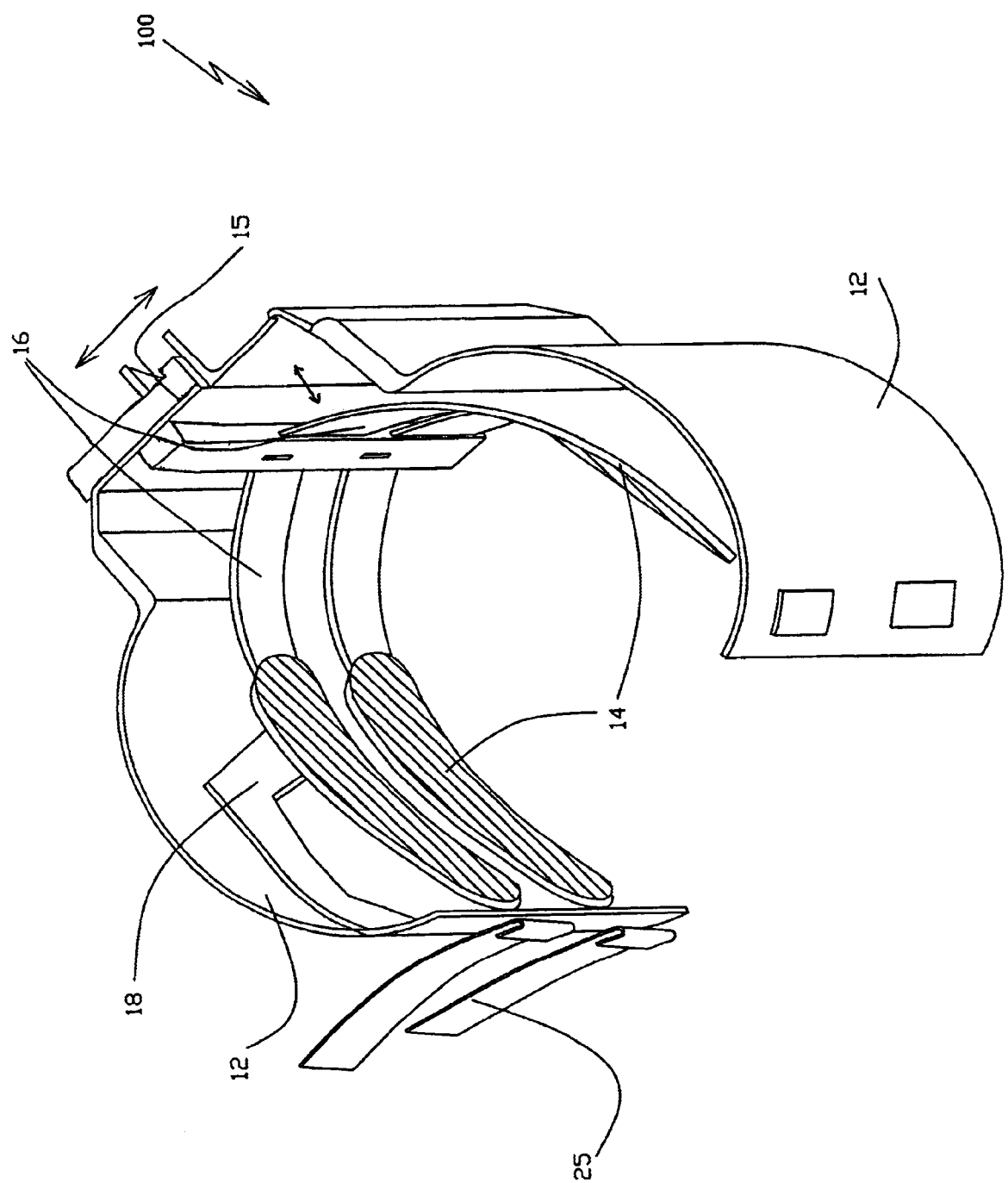
FIG. 3 is a perspective view of another embodiment of an inventive neuroprosthetic device having an adaptive mechanical cushion system, in which the cushion system includes elastic bands.

In FIG. 3, elastic straps 16 for supporting electrodes 14 are anchored in device 100 by strap anchor bar 160. Electrodes 14 are positioned spatially by leaf-spring 18. When device 100 is closed around the limb by means of closure mechanism 15, shells 12 press straps 16 to the limb (not shown). The tension in straps 16 presses electrodes 14 to the limb. The tension in straps 16 is adjusted using tensioning mechanism 25, as needed.

FIGS. 4a and 4b illustrate another embodiment in which cushions 10a to 10d have a rounded surface facing shells 12a and 12b. A cross-sectional cut of the rounded surface is preferably an arc of a circle, oval or ellipse. Cushions 10a to 10d are attached to shells 12a and 12b solely in the middle of the arc, and not along the entire surface of cushions 10a to 10d. Electrodes 14a to 14d, respectively, are attached to cushions 10a to 10d, respectively, along opposite longitudinal edges 26a and 26b. The degrees of freedom between electrode and cushion, and between cushion and shell, provide the inventive device with tremendous flexibility for adapting to changes in limb surface contours as a result of muscle contraction, relaxation, etc. The inherent flexibility of this design enables, upon closing of closure mechanism 15, the formation of an intimate, adaptive contact between electrodes 14a to 14d and the limb (not shown).

FIG. 4a illustrates the device with linear closure mechanism 15 in a closed position. In FIG. 4b, linear closure mechanism 15 is in an open position.

Figure 6A:
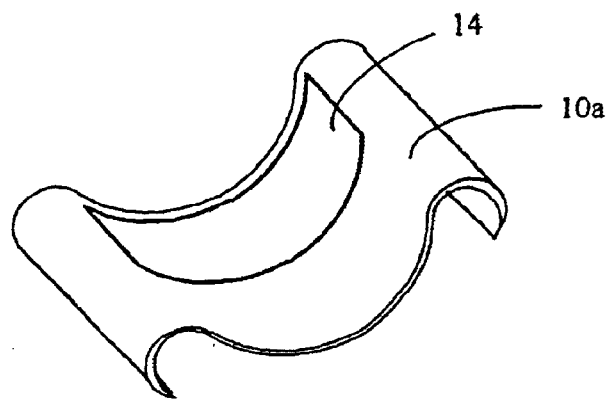
Figure 6B:
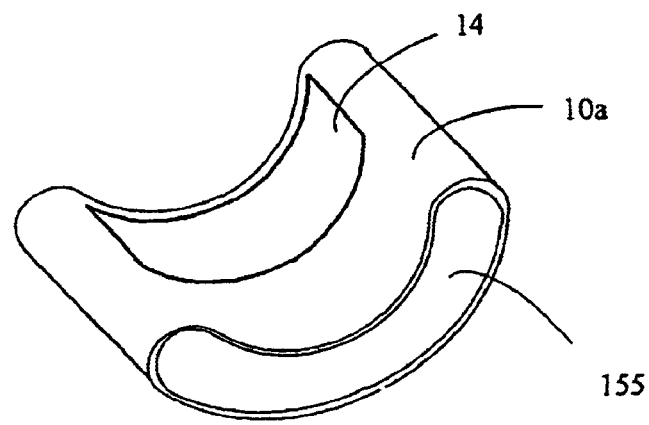
Figure 6C:
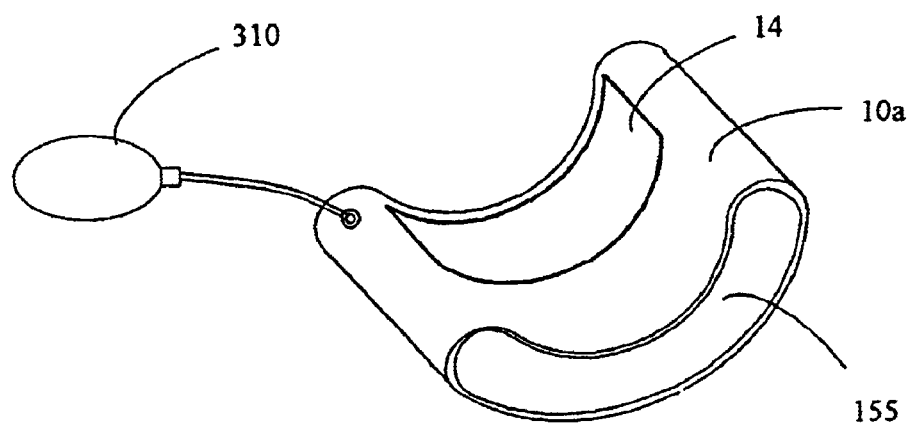

FIGS. 6a–6c are schematic, sectional views of fluid-filled cushion interfaces for use in conjunction with the inventive neuroprosthetic device. Cushion 10a is hollow and may be fluid-filled for supplying the required pressure to maintain contact between the electrode 14 and the skin. A pneumatic cushion may contain air within a trapped, pressurized fluid volume 155 (FIGS. 6b, 6c), or within a volume that fluidly communicates with the environment (FIG. 6a), such that air is free to enter or leave the cushion. In FIG. 6c, air can be pumped into or removed from volume 155 by means of flexible fluid pump 310, which is operatively connected to volume 155.

The cushions used in the device of the present invention may be disposable. The cushion systems are preferably designed such that the cushions can be removed for cleaning, and then reinserted.

The requisite spring characteristics of the cushion are alternatively supplied by mechanical springs (polymer, metal, plastic, etc.) or by a solid filler having a very low modulus of elasticity.

It will be appreciated by those well-versed in the art that various alternative designs of the above-described surface neuroprosthesis device, not described in the exemplary embodiments provided herein, could provide similar improvements in the adaptive flexibility of the device in interfacing with the body site or body limb. For example, the cushion component of the inventive neuroprosthetic device may include an undivided, continuous cushion covering the entire inside of the shell.

As used herein in the Specification and in the claims section that follows, the term "rigid exoskeleton" and the like refer to a substantially-inflexible structure fitting to the outside surface of the body. The term "semi-rigid exoskeleton" and the like refer to a structure having a self-maintaining shape, fitting to the outside surface of the body. The terms are meant to exclude elements not capable of maintaining their own shape such as straps, belts, sleeves, and articles from fabric or cloth.

As used herein in the claims section that follows, the terms "limb", "body limb" and the like, are not limited to arms and legs, and are meant to include other body sites that can benefit from surface neuroprosthetic treatments.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A surface neuroprosthetic system for functional electrical stimulation (FES), having an internal cushion interface, the system device comprising:

a surface neuroprosthesis including:

(a) an at least semi-rigid exoskeleton shell for encompassing at least a portion of a impaired limb, said exoskeleton shell including a mechanism for opening and closing said surface neuroprosthesis;

(b) at least one cushion interface disposed between said shell and said limb, said cushion interface being attached to said shell, and (c) at least one electrical stimulation electrode associated with, and supported by, said cushion interface, said mechanism for providing a compressive force for holding said stimulation electrode to a surface of said limb, wherein said cushion interface of said surface neuroprosthesis is designed and configured to transfer said compressive force from said mechanism to said electrode so as to maintain a continuous electrical contract between said electrode and a skin surface of said limb, thereby providing useful muscular function to said limb, and wherein said cushion interface includes an adaptive mechanical cushion, said adaptive mechanical cushion including at least one mechanical spring, associated with said shell, for providing a pre-determined effective modulus of elasticity.

2. The device of claim 1, wherein said mechanism is configured to transfer pressure to said adaptive mechanical cushion so as to avoid pinching of a soft tissue of said limb.

3. The device of claim 2, further including elastic straps operatively connected to said shell, and wherein said electrode is connected to said straps, such that closing of said mechanism tensions said elastics straps so as to press said electrode to said surface of said limb.

4. The device of claim 1, wherein said adaptive mechanical cushion is adapted to have a substantially similar modulus of elasticity as a local body tissue underlying said skin surface.

5. The device of claim of claim 1, wherein said adaptive mechanical cushion is designed to conform to said surface during contraction and relaxation of muscles of said limb.

6. The device of claim 1, wherein said adaptive mechanical cushion is configured to distribute interactive forces between said cushion interface and said skin surface, so as to maintain a natural contour of said limb.

7. The device of claim 1, wherein said adaptive mechanical cushion includes a solid filler material, so as to achieve said modulus of elasticity.

8. The device of claim 1, wherein said exoskeleton shell is a rigid exoskeleton shell.

9. The device of claim 1, wherein said exoskeleton shell is further designed and configured to be donned using a single hand.

10. The device of claim 1, wherein said adaptive mechanical cushion has a damping constant sufficiently low such that said electrode maintains dynamic contact with said surface during contraction and relaxation of muscles of said limb.

11. The device of claim 1, wherein said mechanism is a linear closure mechanism.

* * * * *